United States Patent [19]

Jimenez et al.

[11] Patent Number: 4,920,983
[45] Date of Patent: May 1, 1990

[54] PHOSPHORESCENT PROPHILACTIC

[76] Inventors: Francisco G. Jimenez, G.P.O. Box 4805, San Juan, P.R. 00936; George Spector, 233 Broadway RM 3815, New York, N.Y. 10007

[21] Appl. No.: 150,843

[22] Filed: Feb. 1, 1988

[51] Int. Cl.⁵ .............................................. A61F 5/44
[52] U.S. Cl. ..................................... 128/844; 604/349
[58] Field of Search ............................... 604/347–353; 128/842–844

[56] References Cited

U.S. PATENT DOCUMENTS

| | | | |
|---|---|---|---|
| 2,410,460 | 11/1946 | Robinson | 604/349 |
| 2,536,631 | 1/1951 | Ely | 604/362 |
| 2,586,674 | 2/1952 | Lonne | 128/844 |
| 4,244,369 | 1/1981 | McAvinn et al. | 604/362 |
| 4,332,243 | 6/1982 | Gutnick | 128/844 |
| 4,432,357 | 2/1984 | Pomeranz | 604/349 |
| 4,446,860 | 5/1984 | Gutnick | 604/844 |

FOREIGN PATENT DOCUMENTS 593637  3/1934  Fed. Rep. of Germany ...... 604/349

OTHER PUBLICATIONS

Everett et al., The Condon Book, May 87, pp. 50-55, 130, 131.

Primary Examiner—C. Fred Rosenbaum
Assistant Examiner—Mark O. Poluth

[57] ABSTRACT

A phosphoresent condom is provided with a bead of phosphoresent liquid located at front end between a pair of sheaths that are one inside the other so that when placed over a regular condom, pressure will brake the bead allowing the phosphoresent liquid to travel and glow between the total length of the sheaths. In another embodiment, the phosphoresent condom is fabricated out of a center layer of colored phosphor material between two sheaths of latex rubber so as to isolate the phosphor material when placed upon a penis.

1 Claim, 1 Drawing Sheet 4,920,983

PHOSPHORESCENT PROPHILACTIC

BACKGROUND OF THE INVENTION

The instant invention relates generally to phrophylatic devices and more specifically it relates to a phosphorescent condom.

Numerous prophylatic devices have been provided in prior art that are each adapted to be a thin rubber sheath designed to cover the penis during sexual intercourse for antivenereal and contraceptive purposes. For example, U.S. Pat. Nos. 3,085,570; 3,136,417 and 3,282,414 all are illustrative of such prior art. While these units may be suitable for the particular purpose to which they address, they would not be as suitable for the purposes of the present invention as heretofore described.

SUMMARY OF THE INVENTION

A primary object of the present invention is to provide a phosphorescent condom that will overcome the shortcomings of the prior art devices.

Another object is to provide a phosphorescent condom that when placed over a regular condom will give off a persistant emission of light following exposure to and removal of incident radiation.

An additional object is to provide a phosphorescent condom that is fabricated out of a center layer of colored phospor material between two sheaths of latex rubber so as to isolate the phosphor material when placed upon a penis.

A further object is to provide a phosphorescent condom that is simple and easy to use.

A still further object is to provide a phosphorescent condom that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
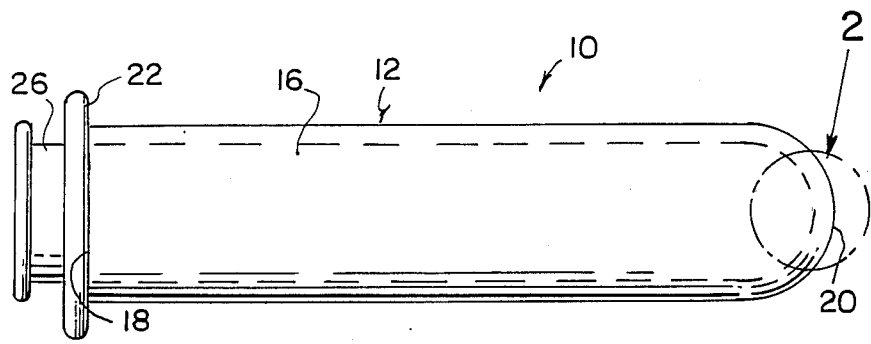
FIG. 1 is a side view of a first embodiment of the invention being a removable glowing sheath placed over a regular condom.
Figure 2:
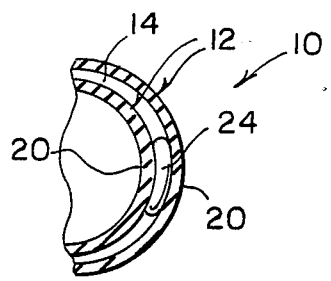
FIG. 2 is an enlarged cross sectional view as indicated by numeral 2 in FIG. 1, showing the sheath being hollow with a bead of phosphorescent liquid placed at the tip which when broken, the phosphorescent liquid will travel and glow throughout the sheath.

Turning now descriptively to the drawings, in which similar reference characters denote similar elements throughout the several views, FIGS. 1 and 2 illustrate a phosphorescent condom 10 consisting of a pair of sheath members 12 one inside the other forming a space 14 therebetween. Each of the sheath members 12 is fabricated out of thin elastic material, having a cylindrical body portion 16 open at rear end 18 and a rounded head 20 closing front end thereof. An annular rim 22 is to seal the rear ends 18 of the pair of sheath members 12 together. A bead of phosphorescent liquid 24 is secured between the pair of sheath members 12 at center of the rounded heads 20 thereof so that when the sheath members 12 are pulled onto a regular condom 26, by the annular rim 22, the bead of phosphorescent liquid 24 will break under pressure to travel and glow throughout the space 14 between the sheath members 12.

Each of the sheath members 12 are fabricated out of latex rubber while the bead of phosphorescent liquid 24 is made in any of a variety of colors for the aesthetic taste.

Figure 3:
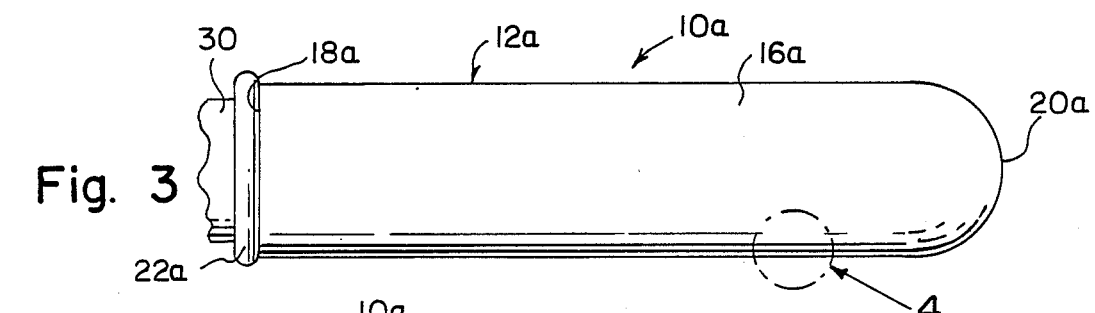
FIG. 3 is a side view of a second embodiment of the invention being made of a center layer of latex rubber impregnated with colored phosphor material between two layers of latex rubber.
Figure 4:
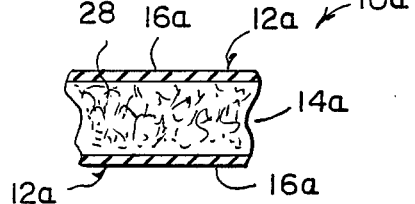
FIG. 4 is an enlarged cross sectional view as indicated by numeral 4 in FIG. 3, showing the layers of material therein.

FIGS. 3 and 4 show another type of phosphorescent condom 10a consisting of a pair of sheath members 12a one inside the other forming a space 14a therebetween. Each of the sheath members 12a is fabricated out of thin elastic material, having a cylindrical body portion 16a open at rear end 18a and a rounded head 20a closing front end thereof. A layer of phosphor material 28 is secured in the space 14a between the pair of sheath members 12a. An annular rim 22 a is to seal the rear ends 18a of the pair of sheath members 12a together so as to isolate the layer of phosphor material 28 when the phosphorescent condom 10a is pulled onto a penis 30 by the annular rim 22a.

Figure 5:
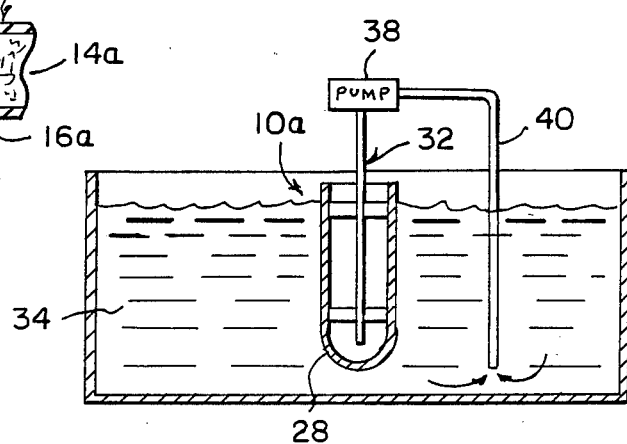
FIG. 5 is a cross sectional view showing how the two layers of latex rubber is placed upon the colored phosphor material.

FIG. 5 shows one way of making the phosphorescent condom 10a. The layer of phospher material 28 in the shape of the condom 10a is positioned onto a perforated tube assembly unit 32 which is placed into liquid latex rubber 34 in a tank 36. A pump 38 that has an elongated intake pipe 40 is attached to the perforated tube assembly unit 32 so that the intake pipe 40 can extend into the liquid latex rubber 34. In this way the pair of sheath members 12a can be formed onto both inner and outer surfaces of the layer of phospor material 28. When the annular rim 22a is formed thereto the complete phosphorescent condom 10a is completed.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A phosphorescent condom having means for distributing a visible phosphorescent substance throughout its extent upon mounting on a penis wherein said means comprises:
   (a) a pair of elastic sheaths, one inside the other forming a space therebetween, said sheaths having rear ends sealed by an annular rim and having spaced rounded heads closing the front ends thereof; and
   (b) a bead of phosphorescent liquid secured between said sheaths at the center of said rounded heads so that when said sheath members are pulled onto a regular condom by said annular rim, said bead will break under pressure to travel and glow throughout the space between said sheaths.

* * * * *